US00PP19070P2

(12) United States Plant Patent
Kaagman

(10) Patent No.: US PP19,070 P2
(45) Date of Patent: Aug. 5, 2008

(54) ***OSTEOSPERMUM* PLANT NAMED 'TRAD PURBILOR'**

(50) Latin Name: *Osteospermum ecklonis*
Varietal Denomination: Trad Purbilor

(75) Inventor: Pim Kaagman, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/821,676

(22) Filed: Jun. 25, 2007

(51) Int. Cl.
*A01H 5/00* (2006.01)

(52) U.S. Cl. ..... Plt./360

(58) Field of Classification Search ..... Plt./360
See application file for complete search history.

(56) References Cited

U.S. PATENT DOCUMENTS

PP15,869 P2 * 7/2005 Dümmen ..... Plt./360

OTHER PUBLICATIONS

UPOV ROM GTITM Computer Database, GTI Jouve Retrieval Software Apr. 2007 Citations For 'Trad Purbilor'.*

* cited by examiner

*Primary Examiner*—Wendy C. Haas
(74) *Attorney, Agent, or Firm*—Jondle & Associates, P.C.

(57) ABSTRACT

An *Osteospermum* cultivar particularly distinguished by purple and white inflorescences, an upright and medium-sized plant habit, and a freely branching and vigorous growth habit, is disclosed.

1 Drawing Sheet

Genus and species: *Osteospermum ecklonis* Norl.
Variety denomination: 'Trad Purbilor'.

BACKGROUND OF THE NEW PLANT

The present invention comprises a new and distinct cultivar of *Osteospermum,* botanically known as *Osteospermum ecklonis* Norl., and hereinafter referred to by the cultivar name 'Trad Purbilor'. The new cultivar originated from a hybridization made in June 1999. The female parent was the proprietary 'OY-85-6' (unpatented) *Osteospermum* plant, with light purple inflorescences, while the male parent was the proprietary 'OY-81-2' (unpatented) *Osteospermum* plant, with purple inflorescences. The seeds produced by the hybridization were sown in August 2003. A single plant selection was chosen for further evaluation and for asexual propagation in January 2004.

The new cultivar was created in 1999 in Andijk, The Netherlands, and has been asexually reproduced repeatedly by vegetative cuttings and tissue culture in Andijk, The Netherlands, Gilroy, Calif. and Hillscheid, Germany over a 2 and a half year period. The present invention has been found to retain its distinctive characteristics through successive asexual propagations.

Plant Breeder's Rights for this cultivar have been applied for in Canada on Mar. 21, 2006 and in Switzerland on Nov. 13, 2006.

SUMMARY OF THE INVENTION

The following are the most outstanding and distinguishing characteristics of the new cultivar when grown under normal horticultural practices in Gilroy, Calif., Andijk, The Netherlands and Hillscheid, Germany.

1. Purple and white inflorescences;
2. An upright and medium-sized plant habit; and
3. A freely branching and vigorous growth habit.

DESCRIPTION OF THE PHOTOGRAPHS

This new *Osteospermum* plant is illustrated by the accompanying photographs which show overall plant habit including inflorescences, buds, and foliage of the plant; the colors shown are as true as can be reasonably obtained by conventional photographic procedures.

DESCRIPTION OF THE NEW CULTIVAR

Figure 1:
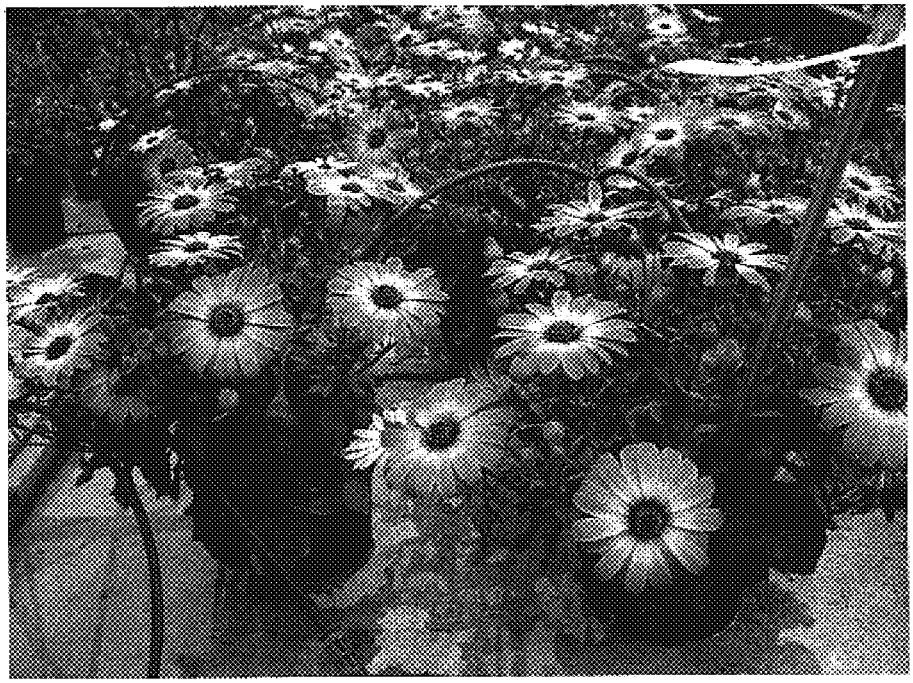
FIG. 1 shows a close-up of a 12-week-old plant grown in a greenhouse in Hillscheid, Germany in May 2006.
Figure 2:
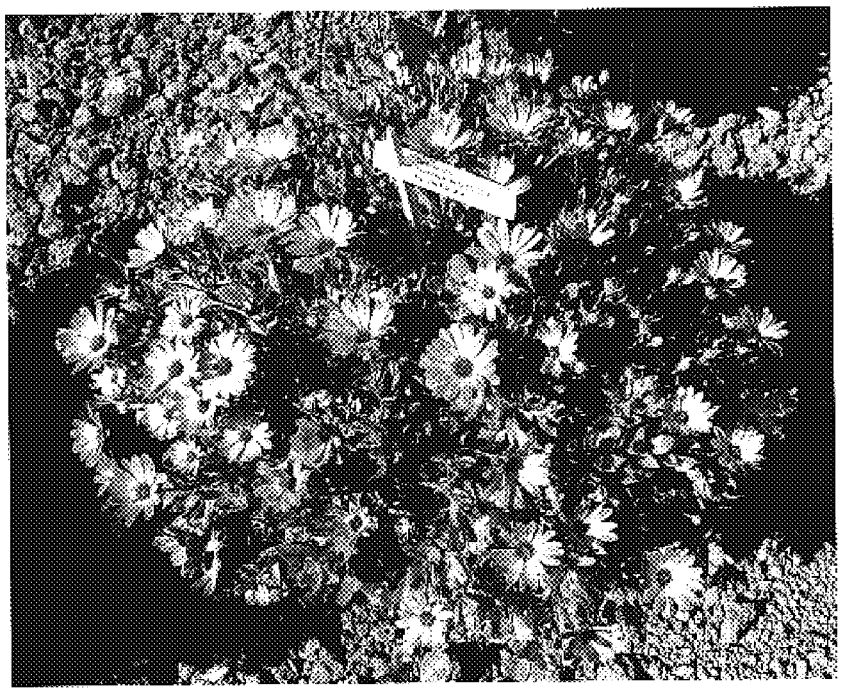
FIG. 2 shows the overall plant habit, including blooms, buds, mature foliage, and the mature inflorescences of a 20-week old plant, grown in France in August 2006.

The following detailed descriptions set forth the distinctive characteristics of 'Trad Purbilor'. The data which define these characteristics were collected from asexual reproductions carried out in Hillscheid, Germany. The plant history was taken on 12-week-old plants, grown in 4-inch pots in a greenhouse during the early spring. The plants had one plant growth regulator treatment and one terminal pinch early in the trial. Color readings were taken under natural light in the greenhouse in March. Color references are primarily to the R.H.S. Colour Chart of The Royal Horticultural Society of London (R.H.S.) (2001). Texture description data was viewed with a dissecting microscope.

DESCRIPTION OF THE NEW PLANT

Classification:
*Family.*—Asteraceae.
*Botanical name.*—*Osteospermum ecklonis* Norl.
*Common name.*—African daisy.

Parentage:

*Female parent.*—The proprietary 'OY-85-6' (unpatented) *Osteospermum* plant having light purple inflorescences.

*Male parent.*—The proprietary 'OY-81-2' (unpatented) *Osteospermum* plant having purple inflorescences.

Plant:

*Form and Habit.*—Herbaceous perennial but usually cultivated as an annual; upright and medium sized.

*Growth and branching habit.*—Vigorously growing, freely branching habit.

*Height* (*from top of soil, including inflorescences*).—15.0 cm to 17.0 cm.

*Width* (*including inflorescences*).—20.0 cm to 23.0 cm.

*Time to produce a finished flowering plant.*—12 to 14 weeks for a 12-cm pot.

*Outdoor plant performance.*—Herbaceous, grown as a perennial for patio planters; used in mixed container planting or garden beds.

*Time to initiate and develop roots.*—24 to 27 days.

*Root description.*—Fibrous, white.

Leaves:

*Arrangement.*—Alternate.

*Shape.*—Oldest, obovate to rhomboid and elliptic-spatulate at the mid-stem.

*Apex.*—Broadly acute.

*Base.*—Attenuate.

*Margin.*—Serrate.

*Texture.*—Leathery, glossy and pilose along the margins and lower surface.

*Fragrance.*—Sharp and spicy.

*Immature leaf.*—Color: Upper surface: RHS 137D to RHS 143A. Lower surface: RHS 143A to RHS 144A.

*Mature leaf.*—Color: Upper surface: RHS 137B. Lower surface: Between RHS 137C to RHS 137D.

*Length.*—5.2 cm to 5.5 cm.

*Width.*—3.3 cm to 3.6 cm.

*Petioles.*—Length: 1.0 cm to 2.0 cm. Diameter: 0.4 cm. Color (both sides): RHS 145B. Texture: Pilose on the side margins.

*Venation.*—Pinnate. Color: RHS 145A.

Stems:

*Total number of branches.*—5 to 8.

*Length.*—9.0 cm to 14.0 cm.

*Diameter.*—3.0 cm to 5.0 cm at midpoint.

*Internode length.*—0.5 cm to 1.0 cm.

*Color.*—Between RHS 143B and RHS 143C.

*Texture.*—Pilose.

*Anthocyanin.*—Absent.

Inflorescence buds:

*Shape.*—Ovate.

*Diameter* (*horizontal*).—0.8 cm.

*Length.*—0.8 cm to 1.2 cm.

*Color* (*just before the ray florets unfold*).—RHS 187B.

Inflorescence:

*Type.*—Capitulum inflorescence, radially symmetrical; terminal and axillary inflorescences held above the foliage.

*Blooming habit.*—Plants flower continuously from spring through fall given the proper growing conditions.

*Quantity of inflorescences per plant.*—20 to 30.

*Lastingness of the inflorescences on the plant.*—11 to 14 days.

*Fragrance.*—Mild (in contrast to the leaves).

*Inflorescence diameter.*—5.8 cm to 6.3 cm.

*Inflorescence depth.*—0.8 cm.

*Disc diameter.*—1.2 cm.

Disc floret:

*Quantity per inflorescence.*—40 to 50.

*Shape.*—Tube-shaped, while the upper end is 5-lobed.

*Tube color* (*immature*).—RHS N88B.

*Tube color* (*mature*).—RHS N79D.

*Length.*—0.5 cm to 0.6 cm.

*Diameter* (*at apex*).—0.2 cm to 0.25 cm.

*Apex.*—Acute.

*Apex color.*—*RHS* 83A.

*Base.*—Fused.

*Margin.*—Entire.

Ray floret:

*Quantity per inflorescence.*—19 to 23.

*Shape.*—Oblanceolate.

*Color.*—Immature: Upper surface: RHS 72D. Lower surface: RHS 77B with a hint of RHS N77A veins. Mature: Upper surface: RHS 76D base color; RHS N78C to RHS N78D towards the apex; RHS N78B basally. Lower surface: RHS 77B with slight stripes of both RHS N77C and RHS N77B, somewhat fading with maturity.

*Length.*—2.8 cm to 3.1 cm.

*Width.*—0.8 cm to 0.85 cm.

*Apex.*—Rounded to obtuse.

*Base.*—Cuneate.

*Margin.*—Entire.

*Texture.*—Papillose and hirsute on the basal margin portions.

*Peduncle.*—Length (from the topmost leaflet): 3.4 cm to 6.0 cm. Diameter: 0.2 cm. Texture: Pilose. Color: RHS 144C to RHS 145A.

Phyllaries:

*Arrangement.*—Whorls at the lower part of the ray florets.

*Observed quantity per plant.*—14 to 16.

*Shape.*—Ligulate.

*Color.*—Upper surface: RHS 137A to RHS 137B; RHS 137C to RHS 137D at the apex; margins are semi-transparent. Lower surface: RHS 138A.

*Length.*—0.9 cm to 1.1 cm.

*Width.*—0.1 cm to 0.15 cm.

*Apex.*—Acute.

*Base.*—Fused.

*Margin.*—Entire.

*Texture.*—Pilose.

Reproductive organs:

*Androecium.*—Location: Present on disc florets only. Stamen quantity: One per disc floret. Stamen color: RHS N78D. Pollen color: RHS 21A. Pollen amount: Moderate.

*Gynoecium.*—Location: Present on ray florets only. Number: One per floret. Pistil length: 0.5 cm to 0.6 cm. Stigma color: Closest to RHS N79A. Style color: Closest to RHS N77B. Style length: 0.3 cm to 0.4 cm.

Fruit and seed set: Seed set not observed.

Disease and insect resistance: Typical of the species; no special observations made.

COMPARISON WITH PARENTAL AND COMMERCIAL CULTIVARS

'Trad Purbilor' differs from the female parent 'OY-85-6' (unpatented) in that 'Trad Purbilor' has purple and white inflorescences, while 'OY-85-6' has light purple inflorescences. Additionally, 'Trad Purbilor' has a more compact plant habit and more branching than 'OY-85-6'.

'Trad Purbilor' differs from the male parent 'OY-81-2' (unpatented) in that 'Trad Purbilor' has purple and white inflorescences, while 'OY-81-2' has purple inflorescences. Additionally, 'Trad Purbilor' has a more compact plant habit and more branching than 'OY-81-2'.

'Trad Purbilor' differs from commercial cultivar 'Westside' (unpatented) in that 'Trad Purbilor' is earlier to flower and has a more purple inflorescence than 'Westside'. Additionally, 'Trad Purbilor' has a more compact plant habit and has shorter peduncles than 'Westside'.

I claim:

1. A new and distinct cultivar of *Osteospermum* plant as shown and described herein.

* * * * *